US007731649B2

(12) United States Patent
Ferrazzi

(10) Patent No.: US 7,731,649 B2
(45) Date of Patent: Jun. 8, 2010

(54) ENDOVENTICULAR DEVICE FOR THE TREATMENT AND CORRECTION OF CARDIOMYOPATHIES

(75) Inventor: Paolo Ferrazzi, Bergamo (IT)

(73) Assignee: Cube S.R.L., Massa (IT)

( * ) Notice: Subject to any disclaimer, the term of this patent is extended or adjusted under 35 U.S.C. 154(b) by 855 days.

(21) Appl. No.: 10/257,500

(22) PCT Filed: Mar. 28, 2001

(86) PCT No.: PCT/IT01/00156

§ 371 (c)(1),
(2), (4) Date: Mar. 31, 2003

(87) PCT Pub. No.: WO01/78625

PCT Pub. Date: Oct. 25, 2001

(65) Prior Publication Data

US 2003/0158570 A1    Aug. 21, 2003

(30) Foreign Application Priority Data

Apr. 13, 2000    (IT)    ............................. PC00A0013

(51) Int. Cl.
*A61M 31/00* (2006.01)
(52) U.S. Cl. ........................................................ 600/16
(58) Field of Classification Search ................. 606/191, 606/237; 600/16, 37; 128/898; 623/1.26, 623/2.34, 1.11, 2.36; 267/167, 168
See application file for complete search history.

(56) References Cited

U.S. PATENT DOCUMENTS

| 2,515,629 | A | * | 7/1950 | Chambers Jr. | ............... 267/167 |
| 4,164,046 | A | * | 8/1979 | Cooley | ....................... 623/2.36 |
| 4,164,064 | A | | 8/1979 | Reavill | |
| 5,117,066 | A | * | 5/1992 | Balsells | ....................... 174/370 |
| 5,228,456 | A | * | 7/1993 | Karg et al. | ................... 128/837 |
| 5,556,414 | A | * | 9/1996 | Turi | ........................... 623/1.11 |
| 5,674,280 | A | * | 10/1997 | Davidson et al. | ........... 623/2.36 |
| 5,776,189 | A | | 7/1998 | Khalid | |
| 5,961,539 | A | | 10/1999 | Northrup | |
| 6,024,096 | A | * | 2/2000 | Buckberg | .................... 128/898 |

(Continued)

FOREIGN PATENT DOCUMENTS

EP    1645244    4/2006

(Continued)

OTHER PUBLICATIONS

Ferrazzi, Paolo et al., "The Titan Can help titln: from micro to macro myocardial elasticity", Journal of Cardiovascular Medicine; 2006, vol. 1. No. 00, pp. 1-6.

(Continued)

*Primary Examiner*—Anhtuan T Nguyen
*Assistant Examiner*—Tuan V Nguyen
(74) *Attorney, Agent, or Firm*—Davidson Berquist Jackson & Gowdey LLP

(57) ABSTRACT

The invention consists in a device that concerns the optimization of the cardiac geometry in patients with heart failure. The device comprises one or more elastic elements in the radial direction towards the inside of the ventricle and plastic deformation in a direction that is transversal to the said ventricle, the element being equipped with means for attaching it to the internal wall of the ventricle.

3 Claims, 5 Drawing Sheets

U.S. PATENT DOCUMENTS

| | | | |
|---|---|---|---|
| 6,217,610 B1 | 4/2001 | Carpentier et al. | |
| 6,264,602 B1 * | 7/2001 | Mortier et al. | 600/16 |
| 6,360,749 B1 * | 3/2002 | Jayaraman | 128/898 |
| 6,425,856 B1 * | 7/2002 | Shapland et al. | 600/37 |
| 6,551,332 B1 * | 4/2003 | Nguyen et al. | 606/151 |
| 6,764,510 B2 * | 7/2004 | Vidlund et al. | 623/2.34 |
| 2003/0045929 A1 | 3/2003 | McCarthy | |
| 2004/0138745 A1 | 7/2004 | Macoviak | |
| 2005/0065601 A1 | 3/2005 | Lee | |
| 2006/0004247 A1 | 1/2006 | Kute | |
| 2006/0074484 A1 | 4/2006 | Huber | |
| 2006/0184241 A1 | 8/2006 | Marquez | |
| 2006/0206203 A1 | 9/2006 | Yang et al. | |
| 2007/0016289 A1 | 1/2007 | Johnson | |

FOREIGN PATENT DOCUMENTS

| | | |
|---|---|---|
| EP | 1854429 | 11/2007 |
| WO | WO 97/26829 | 7/1997 |
| WO | WO 2006/078694 | 7/2006 |
| WO | WO 2006/086434 | 8/2006 |

OTHER PUBLICATIONS

Ferrazzi, Paolo et al., "Implantation of an Elastic Ring at Equator of the Left Ventricle Influences Cardiac Mechanics in Experimental Acute Ventricular Dysfunction," Journal of AMerican College of Cardiology, col. 50, No. 18, 2007.

Ferrazzi, Paolo et al., "The Titan can help titin: from micro to macro myocardial elasticity," Italian Federation of Cardiology, 1558-2027, 2006.

Partial International Search Report mailed Sep. 23, 2009 in PCT/EP2009/059765.

* cited by examiner

 
Fig. 2
 
Fig. 3
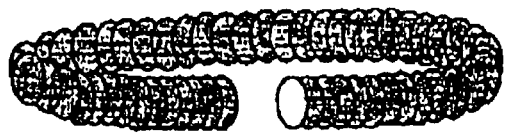 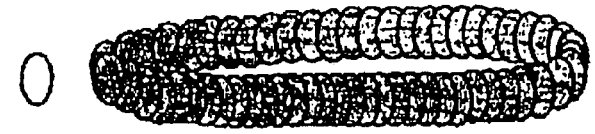
Fig. 4
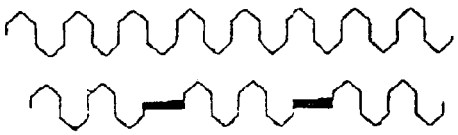
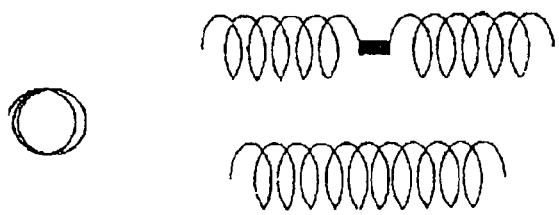
Fig. 5
Fig. 6
Fig. 7
Fig. 8

ENDOVENTICULAR DEVICE FOR THE TREATMENT AND CORRECTION OF CARDIOMYOPATHIES

TECHNICAL FIELD

The present invention is aimed at an endoventricular device applicable to patients affected by heart failure due to a cardiomyopathy of different etiologies (idiopathic, ischemic, valvular), with consequent dysfunction and/or dilatation of the left ventricle with or without mitral insufficiency; the invention likewise concerns a system for optimising the diastolic and systolic activity of a heart affected by a cardiomyopathy. In particular, the invention has to do with an endoventricular device that, in case of cardiomyopathy due to mitral insufficiency with annular dilatation, reestablishes annular dimension and in case of other types of cardiomyopathies, without any mass removal, optimises cardiac geometry as an alternative to transplantation and/or mechanical ventricular assistance, in cases in which the said techniques are not indicated.

PROBLEMS UNDERLYING THE INVENTION

Heart failure is the result of a dysfunction of the heart, particularly cardiac muscle tissue, whose negative effect is that an insufficient blood supply is delivered to the vital organs. This condition of cardiocirculatory insufficiency is a progressive process that can worsen to the point of causing the exitus of the patient.

The cardiomyopathies responsible for the dysfunction have various etiologies (viral diseases, idiopathic cardiomyopathy, valvular diseases, ischemic diseases and congenital diseases).

Cardiomyopathies lead to the dilatation of the heart and its chambers, decreased systolic function (ejection fraction), reduced cardiac output, increased left ventricular wall stress and a consequent increase in end-diastolic pressure.

Over the last twenty years, cardiology and cardiac surgery (perhaps more than other specialist medical disciplines) have achieved extraordinary diagnostic and therapeutic results, and significantly contributed towards prolonging average life expectancy in the more developed countries; these advances have changed the epidemiology of cardiovascular diseases because the prolongation of the average life span has led to an increase in the number of patients affected by heart failure, which is the object of the present invention and can currently be only partially treated. One of the characteristics of heart failure is a progressive deterioration in left ventricular systolic and diastolic function; the mechanism or mechanisms responsible for this progressive hemodynamic alteration are not fully known. but have been partially attributed to a vicious circle in which the physiological mechanisms responsible for the maintenance of homeostasis (hypertrophy and compensatory dilation of the left ventricle, increased rerin-angiotensin and sympathetic nervous system activity) actually accelerate the process of progressive ventricular dysfunction.

Whatever the etiology underlying the dysfunction, it is considered that these compensatory systems lead to a progressive and intrinsic dysfunction in the contractility of cardiomyocvtes and/or an increasing degeneration and loss of the cells themselves. In left ventricular dysfunction, regardless of its etiology, there is therefore an alteration in the structure of the heart and a consequent deformation of cardiac geometry.

A shape other than the physiologically elliptical shape of the left ventricle leads to negative mechanical effects, with an increase in wall tension and the triggering of a counterproductive mechanism of progressive remodeling.

The progressive dilation of the left ventricle leads affected patients from a picture of asymptomatic cardiac dysfunction to one of chronic heart failure.

As mentioned above, heart failure is a rapidly growing epidemiological problem: it is the most common diagnosis in patients aged more than 65 years. and the fourth most frequent cause of hospitalisation in the USA; the syndrome consequently has a substantial economic impact.

Until a few years ago. conventional surgery (that is, coronary artery by-pass grafting and valve replacement) was contraindicated in patients with advanced myocardial dysfunction, and heart transplantation has been acknowledged to be a valid intervention in such cases.

However. the applications of heart transplantation are limited by the small number of donors (10% of cases), and have a large number of relative and absolute contraindications.

DESCRIPTION OF THE STATE OF THE TECHNIQUE

New knowledge and new strategies for the treatment of heart failure have recently proved to be promising.

There is a widely shared cultural belief that patients can be surgically treated in order to improve cardiac function and then subsequently undergo appropriate medical therapy more efficaciously.

In the field of mitral insufficiency with annular dilatation. together with different approaches to valvuloplasty, the usual method adopted for annulus containment is the application of several types of annular rings, all of which are characterized by non-physiological characteristics as rigidity or very partial elasticity.

The most common "conventional" intervention for heart failure in patients with ischemic heart disease is currently coronary artery by-pass grafting (CABG).

The presence of cardiac dysfunction and a clinical picture of heart failure have always been considered risk factors in coronary surgery. New approaches towards preoperative evaluation and perioperative treatment have significantly reduced the mortality associated with such interventions.

The demonstration of ischemia or myocardial viability by means of provocative stress testing makes it possible to expect good results from surgical revascularisation in terms of survival and improved cardiac function.

The same novel concepts in interpreting dysfunction in valvular heart disease have allowed the use of surgery in more severe cases of ventricular dysfunction by means of the application of new methods of myocardial protection and new surgical techniques.

The most striking example is the surgical treatment of mitral valve insufficiency by means of conservative and reparative methods using small prosthetic rings that tend to reduce the posterior annulus and improve the coaptation of the mitral leaflets.

It has been demonstrated that myocardial revascularisation and valve repair are capable of improving left ventricular function.

Recent efforts have concentrated on improving left ventricular function by means of surgical methods aimed at ventriculoplasty with or without a reduction in ventricular volume.

It has been known for some decades that heart failure symptoms in patients with left ventricular aneurysms improve after left ventricular aneurysmectomy.

This concept has also been recently applied to the reconstruction of ventricles with akinetic areas.

Experience has led to the evolution of this type of ventricular reconstruction from the linear repair of the aneurysm to more complicated repairs aimed at excluding infarcted and/or akinetic areas of the septum or free wall. (Jatene-Dor procedure)

Aneurysmectornies and infarctectomies clearly show the functional recovery of the remaining ventricular myocardium, in accordance with the law of Laplace (wall stress=intraventricular pressure ×left ventricle radius/2×wall thickness).

The concept of Laplace has been applied by Batista to the treatment of patients with idiopathic dilated cardiomyopathy or dilated cardiomyopathy of valvular etiology, as well as in Chagas' disease.

Bolling has hypothesised that the application of restrictive annular devices in order to correct the mitral valve insufficiency that is often present in dilated and dysfunctioning ventricles is itself capable of improving cardiac function according to the same principle as that underlying Batista's procedure.

The use of surgical procedures to treat heart failure (in clinical practice or experimentally) is still quantitatively limited; the results are controversial and it is still impossible to define an unequivocally identifiable intervention for the treatment of decompensated patients.

However, it is possible to deduce from clinical results or theoretical interpretations the disadvantages of the techniques so far adopted in clinical practice or experimental settings.

A number of methods and devices have been proposed in order to increase the contractile capacity of the cardiac muscle, limit diastolic volume and reduce cardiac wall stress.

Patent application No. WO9829041 describes a device aimed at treating a decompensated heart by reducing wall stress.

In its main implementation. the device foresees the insertion of a tie-bar designed to draw at least two cardiac chamber walls towards each other; the divulgation also describes a method for positioning the apparatus on the heart.

As will be seen below, in comparison with the present invention, this anterior technique has the drawback that the epicardial application of the tie-bars may interfere with coronary perfusion; furthermore, as the said elements are large pins that constrict two points of the wall. they reduce the diameters of the ventricular section in a linear manner but do not allow a desired reduction distributed throughout the perimeter of the said section.

A further drawback of the device using the anterior technique is that it may cause a subsequent disarrangement and cannot easily be combined with the other corrections required by the disease.

Furthermore. the rigid nature of the tie-bars may interfere with diastolic function. WO9814136 describes a lattice network to be applied to the external surface of the cardiac muscle and the method of application. In comparison with the present invention, this device has the disadvantage that its epicardial application may interfere with coronary perfusion and can cause chronic constrictive pericarditis, as in the case of WO9829041.

Furthermore, the lattice apparently has the same intrinsic disadvantages as those associated with cardiomyoplasty and may interfere with diastolic function The document U.S. Pat. No. 5,192,314 describes an apical cap inserted into the ventricle; however, the said cap does not allow a reduction in equatorial diameter and fails to reach the objective of restoring the optimal geometry of the ventricle.

Patent application No. WO9944534 describes epicardial bands whose drawback is that they may interfere with diastolic function insofar as they may cause greater volumetric constriction, as in the case of the lattice and tie-bars referred to in the other documents mentioned above.

Furthermore, the aforesaid bands make up a static device and do not allow the restoration of optimal ventricular geometry.

In patent application WO9956655 a method (surgical procedure) for left ventricle reshaping is described (similar to the surgical procedures described by Jatene and Dor), using on purpose rigid material without intrinsic properties of elasticity. Therefore it has the same potential disadvantages as the ones quoted for the above mentioned patents and surgical procedures.

In patent application WO0006027 is also described a ring, not attached either to the ventricular wall or to the mitral anulus, that is rigid enough to hold the submitral apparatus with the only purpose of being a restrictive device.

In patent U.S. Pat. No. 5,674,280 a valvular annuloplasty ring is described whose main characteristic is that of being fabricated from a low elasticity metal alloy and therefore with no possible direct activity on ventricular function.

DESCRIPTION OF THE INVENTION

The aim of the present invention is to create a device that makes it possible to overcome the drawbacks of the devices based on the described state of the anterior technique.

It consists of a resilient endocardial device designed to reduce one or more diameters, as well as the volume of the ventricle, by reducing its mitral annulus and/or equatorial circumference and/or apex.

This resilient device has the characteristic of being elastically deformable radially and plastically deformable axially.

The construction characteristics of the said device also have the advantages of allowing a multiple and modular distribution of the aid to systolic function, a gradually increasing resilience that is non-linearly related to end-diastolic pressure, from the systolic to the diastolic phase, thus avoiding greater volumetric constriction and the possible consequence of diastolic interference.

A further advantage of the device of the present invention is that it can be applied without the need to reduce cardiac mass.

Its axial plastic deformability allows its adjustment to the endocardial wall remodeling the left ventricle in the original shape By means of the prosthetic device of the invention, it is possible the reconstruction of optimal cardiac chamber geometry obtaining a wall stress that is modularly redistributed on the prosthetic material and the cardiac wall.

The device is characterised by elastic properties appropriately designed according to a non-linear law.

The said non-linear elasticity allows the device to act as an aid to systolic function during the contraction phase; as far as diastolic function is concerned, the same nonlinear law of elasticity means that the device does not interfere with diastolic function: in fact, although opposing a progressively increasing resistance against dilatation, the said device does not statically constrict the heart by impeding its expansion within physiological limits, as in the case of the devices described in WO9814136 and WO9944534.

It is possible to combine the implantation of this device with other epicardial and intracardiac procedures (mitral valvuloplasty, mitral valve replacement, aortic valve replacement, CABG, etc) made necessary by the disease, and it is likewise possible to personalise the ventricular remodeling on the basis of the functional. volumetric and geometric characteristics of the patient's ventricle by using the device in different ways (in different numbers and sizes).

DESCRIPTION OF THE FIGURES

The figures make it possible to understand better the inventive aspects of the device.

FIG. 2 shows a first type of device;

FIG. 3 shows a second type of device;

FIG. 4 shows a third type of device;

FIG. 5 shows a fourth type of device;

FIG. 6 shows a fifth type of device;

FIG. 7 shows a sixth type of device;

FIG. 8 shows a seventh type of device;

FIG. 1 shows a ventricular cavity/left ventricle 1 in which, at the top, the aorta 9 is visible; the devices of the present invention are inserted on the endocardium 2 of the ventricular cavity 1, and consist of devices 6, 7 or 8, which are substantially elliptical, circular or asymmetrical in shape (see FIGS. 2-8) and are in any case adjustable to different sections 3, 4 or 5 of the internal perimeter of the endocardium 2, in a number depending on the characteristics of the dysfunctioning ventricle.

Without modifying the functioning underlying the present invention, the devices may have different shapes and different sections. They may likewise be open or closed, as shown respectively from FIG. 2 to FIG. 8. in order to leave free the normally functioning areas of the ventricle.

The different sizes of the said devices depend on the dimensions of the ventricle and also on the different diameters of sections of the same ventricle.

Figure 1:
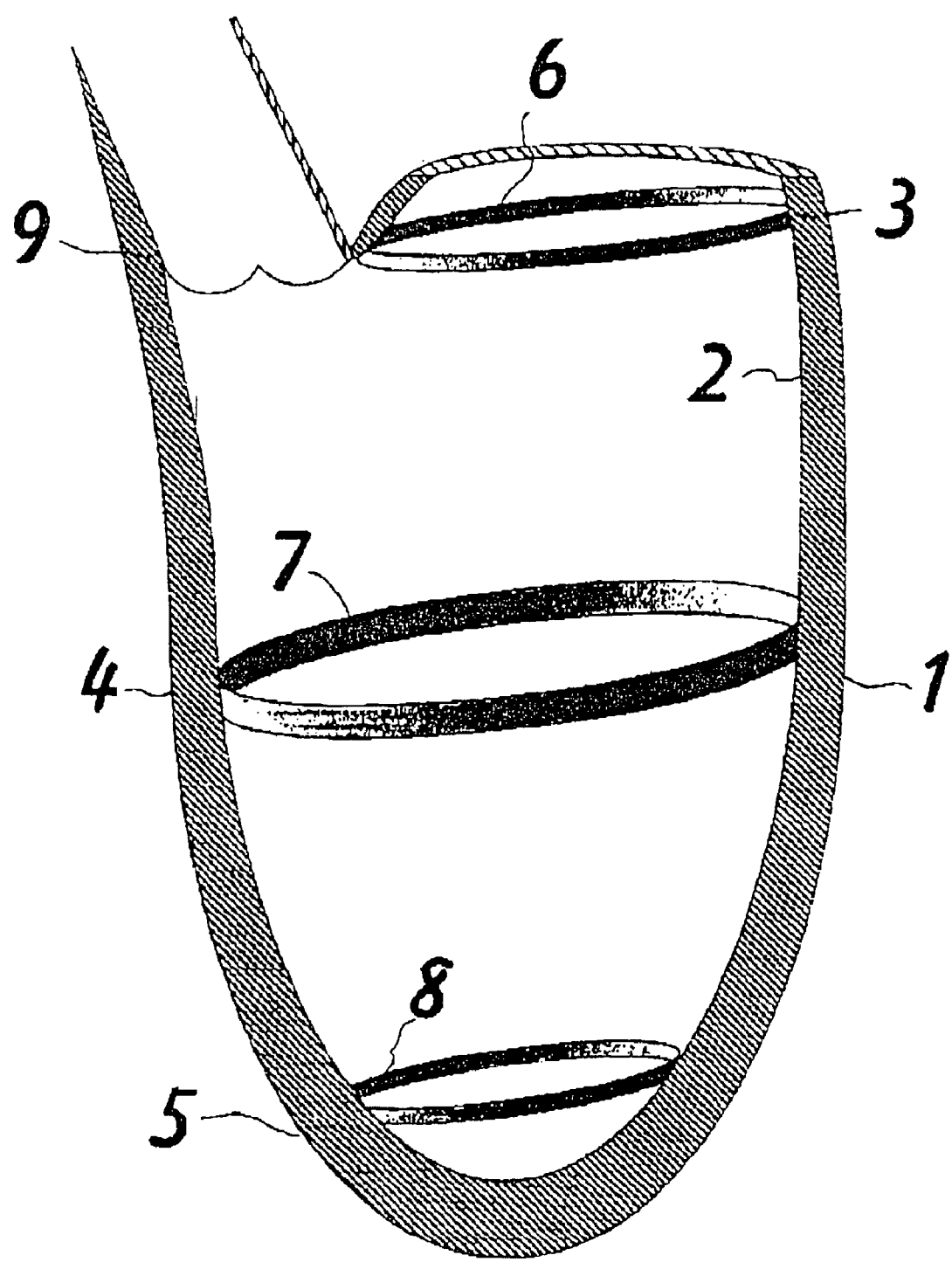
FIG. 1 is a cross-section of a ventricular cavity, with the device located in various positions.

In fact, with reference to FIG. 1. device 6 can be positioned on the diameter relating to the mitral annulus 3, or device 7 can be positioned on an equatorial diameter 4. and device 8 can be positioned on the apical diameter 5.

With reference to FIG. 2. the devices have a solid rectangular section. visible in the centre. and may be an open band, as shown on the left, or a closed ring, as shown on the right.

With reference to FIG. 3, the devices have a solid circular section, visible in the centre, and may be an open band. as shown on the left, or a closed ring, as shown on the right.

With reference to FIG. 4, the devices have a hollow bellows-like circular section, visible in the centre, and may be an open band, as shown on the left, or a closed ring, as shown on the right.

With reference to FIG. 5, the devices are made as open or closed bands in the form of a flat spring, which may be continuous or discontinuous.

With reference to FIG. 6, the devices are made as open or closed bands in the form of a helicoid spring, which may be continuous or discontinuous.

As already said, the devices are plastic in the direction of the axis of the ventricle (see FIGS. 7 and 8) and elastic in the direction of the ventricular radius: this leads to an active diastolic expansion in which the resilience of the device, under endoventricular pressure. allows its radial dilatation to a predetermined useful extent and the simultaneous accumulation of elastic energy: at its maximum load. the device returns to its resting dimensions, thus operating an active systolic return as a result of its elastic force.

The function of elasticity illustrated by the devices is not linear because, in the diastolic phase, they must oppose little resistance against expansion; the elasticity of the material must diminish in an inverse relationship with endoventricular pressure in such a way as to ensure that the device opposes greater resistance to dilation as it expand towards its maximum diameter, which coincides with the maximum value of end-diastolic pressure.

The device charged with elastic energy will invert its direction of movement from this point of maximum dilatation and begin to contract: being sutured to the endocardial wall of the ventricle or running through the myocardial wall, it will exercise a direct inward force on the wall itself that will aid the contraction of the ventricle (systolic phase).

Figure 9:
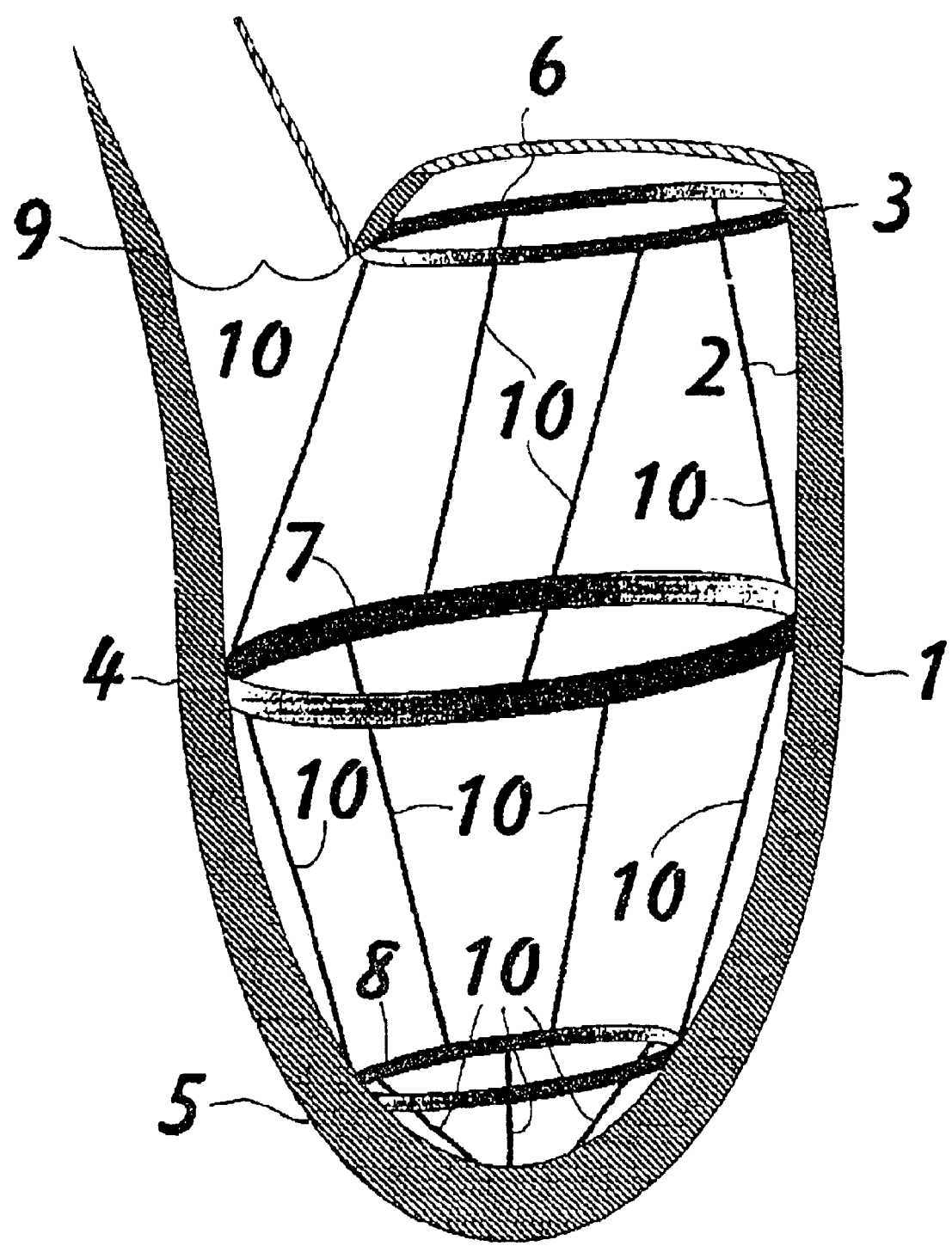
FIG. 9 shows a cross-section of a ventricular cavity with devices connected by axial elastic elements.

In the implementation shown in FIG. 9, the devices 6, 7 and 8 are connected by means of elastic elements 10 in order to produce forces of a predetermined intensity along the axis of the ventricle 1; the said forces may be symmetrical or asymmetrical. The elastic elements 10 are attached to devices 6, 7 and 8 or sutured to the walls of the ventricle 1.

Figure 10:
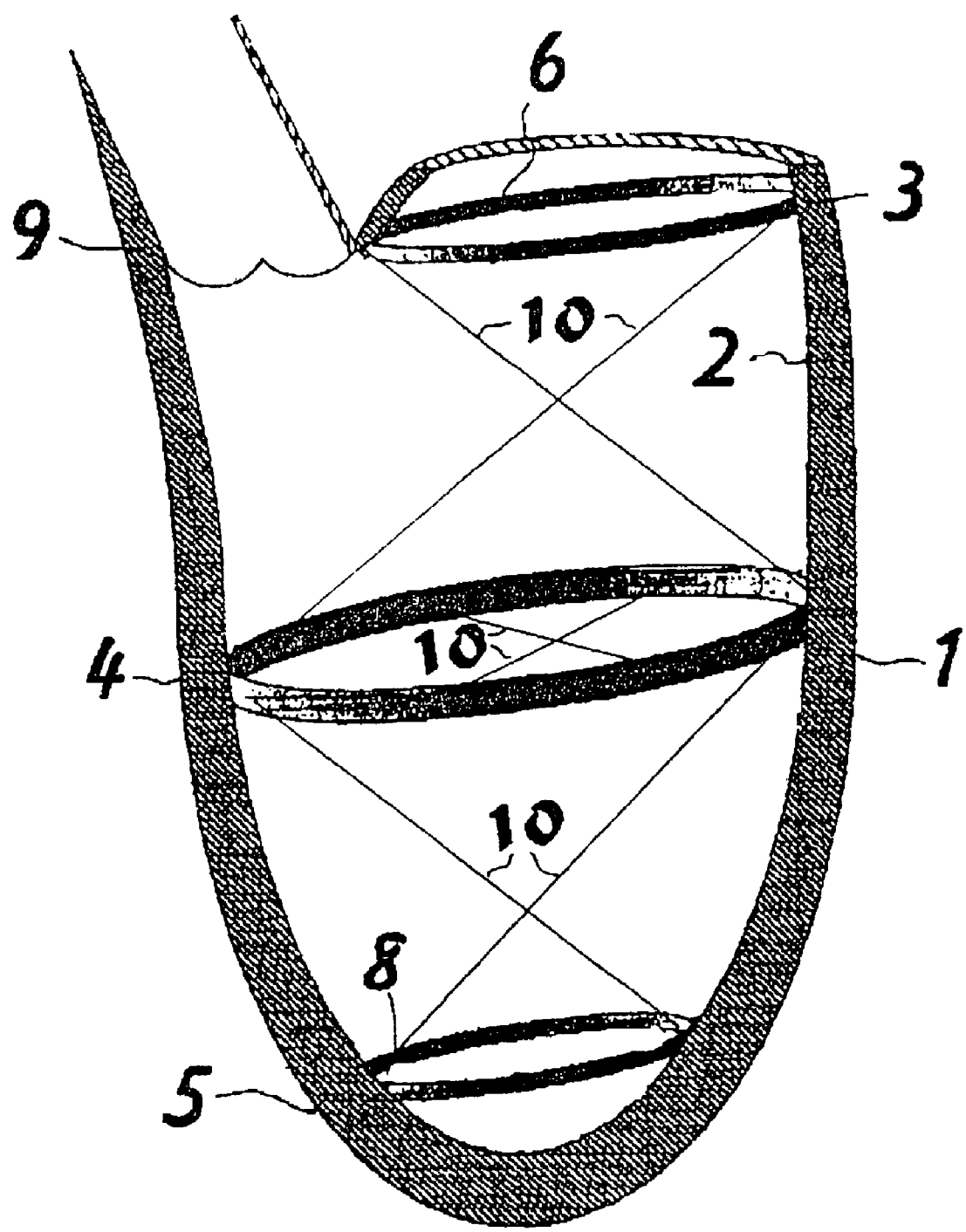
FIG. 10 shows a cross-section of a ventricular cavity with devices connected by elastic elements having axial and radial components.
Figure 11:
FIG. 11 shows a device with a covering.
Figure 12:
FIG. 12 shows another type of device with a covering
Figure 13:
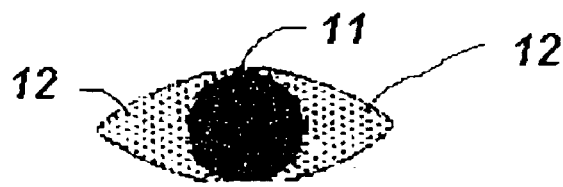
FIG. 13 shows another type of device with a covering.
Figure 14:
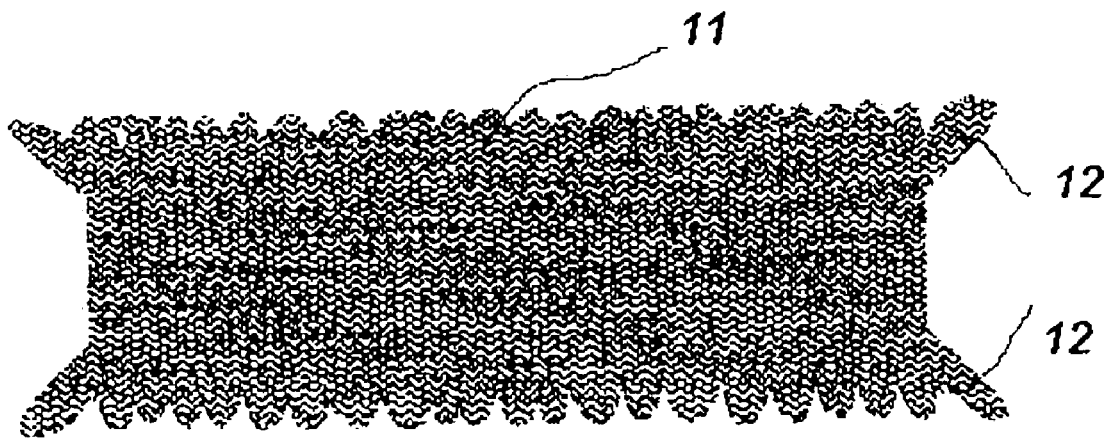
FIG. 14 shows the means of fixing the device.

With reference to FIG. 10, the devices 6, 7 and 8 are connected at various points of their circumference by means of elastic elements 10, whose radial and axial components are designed to produce forces of a predetermined intensity.

In a preferential implementation, with reference to FIGS. 10, 11, 12 and 13, they are constructed of biocompatible material covered by a sheath or woven covering of biological or biocompatible material presenting two lips or lateral flaps suitable for suturing; the material constituting the said woven covering can be, for example, autologous pericardium or heterologous pericardium, or a non-thrombogenic biocompatible material of the types already existing on the market (teflon, dacron, silicone).

It is also possible to construct the devices of biocompatible material of the invention in such a way that their transversal dimensions vary along the perimeter, narrowing in parts that are suitable for being directly sutured to the endocardium without the need for the sheath.

The method of application of the said devices is to suture the lips of the covering sheath using detached stitches, possibly U-shaped, reinforced with pladgets of dacron or another biological material of the type described.

Using this method, the stitches do not interfere with the elastic and flexible element making up the prosthetic device.

The suturing must be complete: that is, two circumferential sutures of detached stitches for each device. unless the stitches have to be transmural.

Another method of application of the device is that of a mattress suture accomplished with the open ring/band itself running through the thickness of the muscular wall and the junction of the tips at a predetermined measure.

The sutures applied for the longitudinal and transversal connection of the prosthetic elements are made with a predetermined elasticity.

Any component of the device must be characterized by radioopacity by means of intrinsic radioopacity of the material used (metal spring) or the addition of radioopaque elements inside the elastic material or the coverage material.

By means of the described device, the following objectives are reached:
(a) an increase in the ejection fraction, by which is meant the ratio between the enddiastolic volume and the difference between end-diastolic volume and end-systolic volume,
(b) the elimination of mitral valve insufficiency by maintaining the physiological elasticity of the native annulus,
(c) an aid to systolic function using the intrinsic force of the device,
(d) pre-modulated diastolic expansion, and
(e) chronic radiographic control of the device function and its relationship with the cardiac function.

It can be directly derived that the present invention is suitable for different shapes and implementations of the device, while remaining within the ambit of the same inventive concept.

The invention claimed is:

1. An endocardial heart function intervention device comprising, at least one ring shaped device from a set of three ring shaped devices having substantially elliptical, circular and asymmetrical body shapes, respectively, said at least one device having transversal dimensional variations comprising resilient portions and formed connection portions at spaced apart locations along the device at so that the device is configured to be engagable with and connectable within a heart and onto an endocardium wall, each shaped device being formed as an elastic structure having flexibility along an axis of a ventricular cavity and having radial elasticity during the diastolic phase which diminishes inversely with endoventricular pressure so that each device, when connected in place, can be adjusted to a section of the endocardial wall at a neutral rest position and can thereafter expand to receive energy from the endocardial wall during a first part of a diastolic phase, and to cede energy received to the endocardial wall during a first part of a systolic phase, wherein the intervention device comprises a set of three ring shaped devices, each of said rings in the set having one of an elliptical, circular or asymmetrical shape and the three ring shaped devices are interconnected together within the heart.

2. An endocardial heart function intervention device comprising, at least one ring shaped device from a set of three ring shaped devices having substantially elliptical, circular and asymmetrical body shapes, respectively, said at least one device having transversal dimensional variations comprising spring portions and formed connection portions at spaced apart locations along the device at so that the device is configured to be engagable with and connectable within a heart and onto an endocardium wall, wherein the formed connection portions are dimensionally different from the spring portions within the body shapes, each ring shaped device being formed as an elastic structure having flexibility along an axis of a ventricular cavity and having radial elasticity during the diastolic phase which diminishes inversely with endoventricular pressure so that each device, when connected in place, can be adjusted to a section of the endocardial wall at a neutral rest position and can thereafter expand to receive energy from the endocardial wall during a first part of a diastolic phase, and to cede energy received to the endocardial wall during a first part of a systolic phase, wherein the intervention device comprises a set of three ring shaped devices, each of said rings in the set having one of an elliptical, circular or asymmetrical shape and the three ring shaped devices are interconnected together within the heart.

3. An endocardial heart function intervention device comprising, at least one ring shaped device from a set of three ring shaped devices having substantially elliptical, circular and asymmetrical body shapes, respectively, said at least one device having transversal dimensional variations comprising spring portions and formed connection portions at spaced apart locations along the device at so that the device is configured to be engagable with and connectable within a heart and onto an endocardium surface, with the formed connection portions having a different shape from the remainder of the at least one ring shaped device, each ring shaped device being formed as an elastic structure having flexibility along an axis of a ventricular cavity and having radial elasticity during the diastolic phase which diminishes inversely with endoventricular pressure so that each device, when connected in place, can be adjusted to a section of the endocardial wall at a neutral rest position and can thereafter expand to receive energy from the endocardial wall during a first part of a diastolic phase, and to cede energy received to the endocarcdial wall during a first part of a systolic phase, wherein the intervention device comprises a set of three ring shaped devices, each of said rings in the set having one of an elliptical, circular or asymmetrical shape and the three ring shaped devices are interconnected together within the heart.

* * * * *